United States Patent

Kwiatkowski et al.

Patent Number: 5,609,580
Date of Patent: Mar. 11, 1997

[54] INJECTION HOLDER FOR A PLUNGERLESS SYRINGE AND COMBINATION PLUNGERLESS SYRINGE AND INJECTION HOLDER

[75] Inventors: Edward J. Kwiatkowski, Denville; David G. Swaim, Bradley Beach, both of N.J.

[73] Assignee: Vital Signs, Inc., Totowa, N.J.

[21] Appl. No.: 502,062

[22] Filed: Jul. 14, 1995

Related U.S. Application Data

[63] Continuation-in-part of Ser. No. 307,077, Sep. 16, 1994.
[51] Int. Cl.$^6$ ................................ A61M 5/178
[52] U.S. Cl. .................... 604/212; 604/216; 604/232; 604/235
[58] Field of Search .................... 604/212, 216, 604/200, 217, 214, 228, 185, 187, 232–235, 403, 404, 407, 408, 410

[56] References Cited

U.S. PATENT DOCUMENTS

| | | | |
|---|---|---|---|
| 2,667,163 | 1/1954 | Smith | 604/214 X |
| 2,674,247 | 4/1954 | McLellan | 604/213 X |
| 3,144,178 | 8/1964 | Sarnoff | 604/235 X |
| 3,220,412 | 11/1965 | Mcconnaughey et al. | 604/235 |
| 3,340,869 | 9/1967 | Bane | 604/216 |
| 3,811,441 | 5/1974 | Sarnoff | 604/232 X |
| 3,848,593 | 11/1974 | Baldwin | 604/232 X |
| 4,236,516 | 12/1980 | Nilson | 604/214 |
| 4,282,986 | 8/1981 | af Ekenstam et al. | 604/212 X |
| 4,410,323 | 10/1983 | Hodosh et al. | 604/212 |
| 5,242,422 | 9/1993 | Schneberger et al. | 604/216 |
| 5,451,214 | 9/1995 | Hajishoveh | 604/235 |

*Primary Examiner*—Vincent Millin
*Assistant Examiner*—V. Alexander
*Attorney, Agent, or Firm*—R. Gale Rhodes, Jr.

[57] ABSTRACT

Combination plungerless syringe and ejector for applying force to the bellows portion of the syringe to eject liquid received by the syringe through the cannula portion of the syringe; the injector includes a receptacle generally complementary in shape to and for releasably receiving at least the bellows portion of the syringe. Injector for injecting liquid from a plungerless syringe which includes a cannula portion and a bellows portion, the injector includes a receptacle generally complementary in shape to and for receiving at least the bellows portion of the syringe.

19 Claims, 6 Drawing Sheets

INJECTION HOLDER FOR A PLUNGERLESS SYRINGE AND COMBINATION PLUNGERLESS SYRINGE AND INJECTION HOLDER

CROSS-REFERENCE TO RELATED APPLICATIONS

This application is a continuation-in-part of U.S. patent application Ser. No. 08/307,077, filed on Sep. 16, 1994, now pending, entitled PLUNGERLESS SYRINGE, David G. Swaim inventor, and which application is assigned to the same assignee as the present application.

BACKGROUND OF THE INVENTION

1. Field of the Invention

This invention relates generally to combination apparatus for ejecting or expelling fluid and more particularly relates to the combination of a plungerless syringe for expelling or injecting a fluid in a substantially bubbleless manner thereby substantially eliminating the threat of an air-embolism and an injector, injector holder or ejection force applying means for applying fluid ejection force to a plungerless syringe. This invention also relates to an injector, injector holder or ejection force applying means for applying fluid ejection force to a plungerless syringe.

2. Description of the Prior Art

Syringes are well known to the art which include a substantially transparent plastic cylindrical tube providing a fluid receiving chamber, a plastic plunger mounted slidably in one end of the tube and a metal needle mounted to the other end of the tube. The plunger is withdrawn to create a vacuum and draw fluid into the chamber after which the plunger is forced into the chamber to expel or eject the fluid through the needle. Typically, the plunger and cylindrical member are disposable, but the metal needle typically is reusable and must be removed from the tube for resterilization prior to reuse. Removal of the needle is well known for the possibility of the user being pricked or stuck by the needle with the highly undesirable attendant possibility of infectious disease transmission.

Plungerless syringes are known to the art, such as for example the plungerless syringe disclosed in U.S. Pat. No. 5,102,398, entitled PLUNGERLESS SYRINGE, and patented Apr. 7, 1992, Barry L. Farris inventor. This plungerless syringe is disclosed as providing substantially bubbleless fluid ejection or expulsion by the employment of an air chamber attached to the bellows portion of the syringe and which air chamber is taught as being for entrapping air contained in the fluid.

As further known to those in the art, the plunger of the prior art plunger syringe, noted above, is initially partially depressed to expel some fluid from the syringe so as to purge air from the adapter or fluid delivery device, such as a needle or catheter, to which the syringe is connected thereby reducing, or substantially eliminating, the possibility of the injection of air into a person's blood stream with the attendant possible air embolism. The construction of the typical prior art plungerless syringe is such that it does not lend itself to two distinct stages of fluid expulsion including a first stage for ejecting or expelling a portion of the fluid in the syringe to purge air from the delivery system and a second stage for ejecting or expelling the remaining fluid contained in the syringe.

Accordingly, there exists a need for a plungerless syringe providing for two stages of collapse, an initial or purge stage where air contained in the fluid delivery device to which the syringe is attached is purged, and a second flush stage where the remaining fluid in the syringe is expelled.

The prior art plunger syringe, noted above, is also used to determine whether the needle has been properly inserted into a blood vessel of a patient. This is accomplished by partially depressing the plunger to expel a portion of the fluid contained in the syringe after which the plunger is withdrawn to reflux the previously expelled fluid and to withdraw a blood sample into the transparent syringe which provides a visible determination that the tip of the needle is in fact in a blood vessel. The plungerless syringes known to the prior art do not include any structure permitting such fluid reflux and blood sample withdrawal and hence cannot be used to determine if the needle tip is properly inserted into a blood vessel.

Accordingly, there exists a need for a plungerless syringe provided with structure permitting the reflux of previously expelled fluid and a blood sample to determine whether the tip of the needle attached to the plungerless syringe is properly inserted into a blood vessel.

Still further, the typical prior art plunger syringe is relatively expensive to manufacture because it must be manufactured in several steps and assembled and frequently lubrication is required.

Accordingly, there exists a need in the art for a plungerless syringe which is relatively inexpensive to manufacture, contains no moving parts making the plungerless syringe suitable for radiation and sterilization.

Injectors or injector holders are known to the art for facilitating the operation of syringes provided with a plunger.

Figure 4:
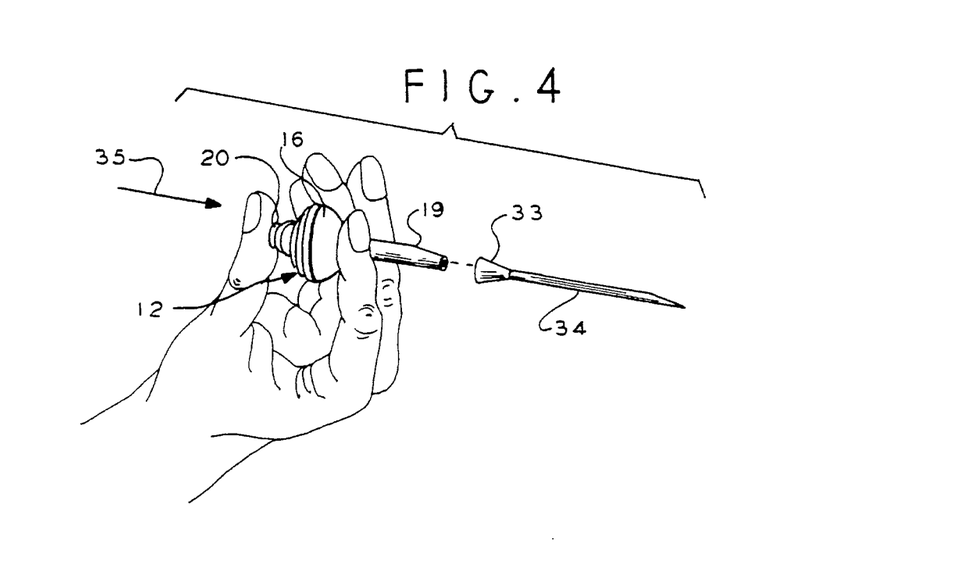
FIG. 4 is a diagrammatical view illustrating the manner in which the plungerless syringe of the present invention is held by a user to collapse of the bellows portion of the syringe to expel or inject fluid into a fluid delivery device such as a needle.

Although plungerless syringes can be operated directly by a user as illustrated in FIG. 4 and described below, it has been found that it can be beneficial to the user to provide an injector or injector holder for facilitating operation of a plungerless syringe.

Accordingly, there exists a need in the art for combination plungerless syringe and injector or injector holder and a need in the art for an injector or injector holder for facilitating operation of a plungerless syringe.

SUMMARY OF THE INVENTION

Combination plungerless syringe and ejection force applying means for applying force to the bellows portion of the syringe to eject liquid received by the syringe through the cannula portion of the syringe; the injection force applying means includes receptacle means generally complementary in shape to and for releasably receiving at least the bellows portion of the syringe.

Injector apparatus for injecting liquid from a plungerless syringe which includes a cannula portion and a bellows portion, the injector apparatus including a receptacle generally complementary in shape to and for receiving at least the bellows portion of the syringe.

DESCRIPTION OF THE PREFERRED EMBODIMENT

Figure 1:
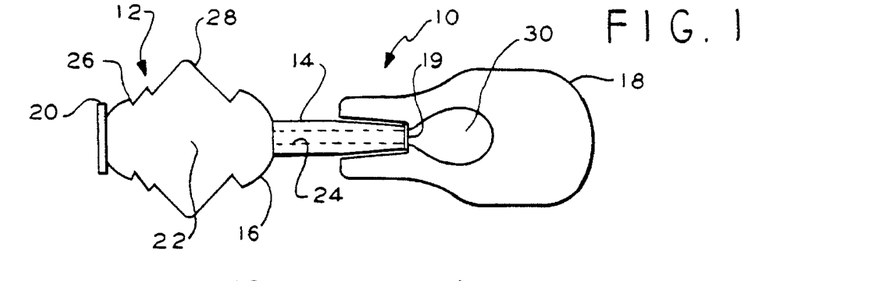
FIG. 1 is a side view of a plungerless syringe embodying the present invention.
Figure 2:
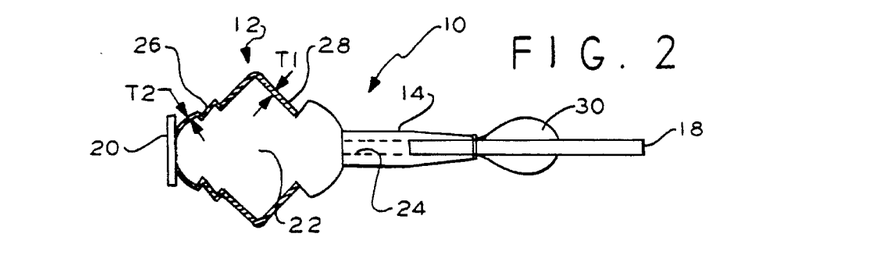
FIG. 2 is a side view showing the plungerless syringe of FIG. 1 rotated 90°.
Figure 3:
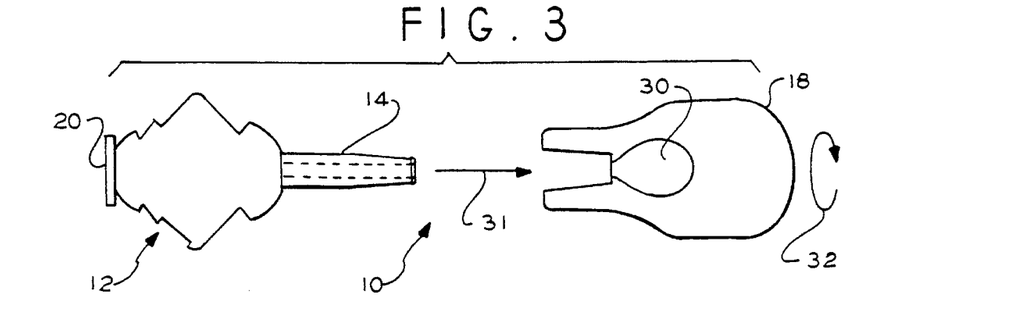
FIG. 3 shows the tab portion removed from the bellows and cannula portions of the plungerless syringe.

Referring to the drawings and in particular to FIGS. 1–3, a plungerless syringe embodying the present invention is shown and indicated by general numerical designation 10; the plungerless syringe is particularly useful for expelling or injecting fluids, viz. such as a saline solution, drugs or other fluids or liquids typically injected by a syringe into a needle or catheter. The syringe 10 includes a rearward hollow, collapsible, bellows portion indicated by general numerical designation 12, a forward cannula portion 14, a generally semi-spherical dome portion 16 intermediate the bellows portion 12 and the cannula portion 14 for substantially receiving the bellows portion upon being collapsed and decreasing in diameter toward the cannula portion, a removable or break-away tab 18 initially secured or sealed to the outer tip 19 of the cannula portion 14 and a rearward disk-like or push-button portion 20 which is also referred to hereinafter as tab 20. The bellows portion 12 provides an internal or bellows chamber 22 for receiving fluid to be expelled or injected and the cannula portion 14 includes a passageway 24 in fluid communication with the internal chamber 22 and through which passageway fluid contained in the chamber is expelled upon the bellows portion 12 being collapsed. The bellows portion 12 includes a first or rearward bellows portion 26 and a second or forward bellows portion 28 and is made of a suitable substantially transparent flexible plastic material described in detail below. The tab 18 provides an over-fill chamber 30 in fluid communication with the cannula passageway 24 and the internal bellows chamber 22 and which over-fill chamber 30 permits the over-filling of the internal bellows chamber 22 and the cannula passageway 24 with fluid in the manufacture of the syringe 10 and isolates the head space inherent in any fluid filling operation to the over-fill chamber 30. AS will be described in detail below, this isolation of the head space is particularly beneficial in the substantial elimination of the risk of an air embolism because it eliminates head space in the bellows chamber 22 and the cannula passageway 24 which head space is inherent in any fluid filling operation such as when the plungerless syringe is filled with fluid. Thus, it will be understood, when the tab 18 is removed from the cannula portion 14 by being pulled away as indicated by the arrow 31 and twisted as indicated by the arrow 32 in FIG. 3, the tab portion is removed from the cannula portion and the bellows chamber 22 and cannula passageway 24 are fluid-filled and ready for use.

The cannula tip 19 is formed in the shape of a male luer connector so as to be compatible with a female luer connector typically provided at the hub of a needle or catheter.

Referring to FIG. 4, upon the tab 18 being removed as shown in FIG. 3 and described above, the user grasps or holds the bellows portion 12 by placing the index and middle finger around the dome portion 16 and by placing the thumb on the push-button 20. The cannula tip 19 may be previously inserted into the hub portion 33 of the needle 34 and the user's thumb is pressed inwardly to apply inwardly acting force indicated by the arrow 35 in FIG. 4 to compress the bellows portion 12 and expel fluid from the syringe into and through the needle 34.

Figure 5:
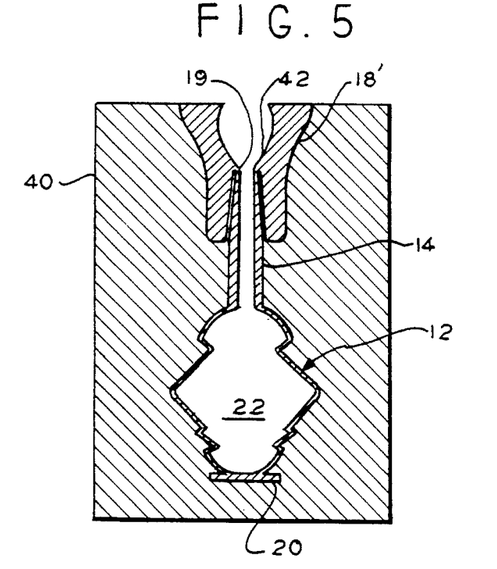
FIG. 5 is a vertical cross-sectional view of a mold illustrating the forming of a portion of the plungerless syringe.
Figure 6:
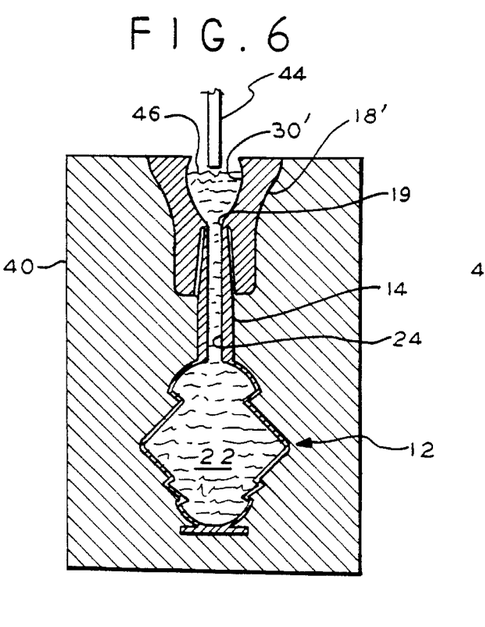
FIG. 6 is a vertical cross-sectional view illustrating the filling of a portion of the plungerless syringe.
Figure 7:
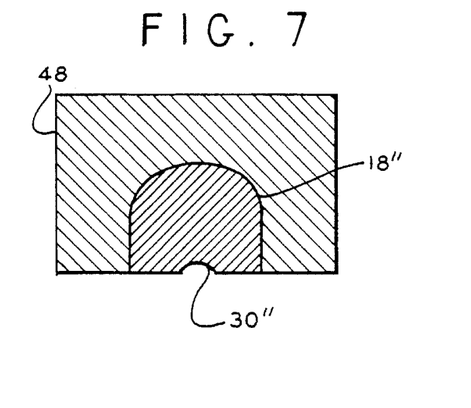
FIG. 7 is a vertical cross-sectional view of a mold illustrating the forming of a second portion of the plungerless syringe.

Referring now to FIGS. 5–8 and first to FIG. 5, the plungerless syringe 10 of the present invention may be manufactured in three stages from substantially transparent polyethylene, polypropylene, or blends thereof, or other flexible resin, to make the syringe 10 substantially transparent permitting the user to observe fluid within the bellows chamber 22, the cannula passageway 24 and the over-fill chamber 30; such transparency also permits the user to observe the intentional reflux of fluid into the syringe and the withdrawing of blood from a blood vessel determining that the tip of the needle connected to the syringe is properly inserted into a blood vessel. A first stage of manufacture is illustrated in FIG. 5 wherein the bellows portions 12, cannula portion 14, push-button portion 20 and a portion 18' of the removable tab 18 are formed from the noted plastic materials in a suitable mold 40 such as, for example, by a suitable blow molding operation. It will be particularly noted that the tab portion 18' includes an inner portion 42 which is formed integrally with the cannula tip 19 thereby initially attaching or mounting the tab portion 18 to the cannula tip 19. It will be understood that the tab portion 42 and the cannula tip 19 are formed integrally in a relatively thin circular ring-like portion, or frangible edge, which may be readily broken to remove the tab 18 from the cannula tip 19 as shown in FIG. 3 and described above.

After the first manufacturing stage illustrated in FIG. 5, suitable filling apparatus, not shown except for a filling tube 44, is placed over the mold 40 and the internal bellows chamber 22, the cannula passageway 24, and a portion 30' of the over-fill chamber 30 (FIGS. 1–3) are filled with a suitable injectable fluid 46 of the type noted above. It will be noted particularly that the top or fill line of the fluid 46 resides above the cannula tip 19 and resides in the portion 30' of the over-fill chamber 30. Thereafter the fluid filling apparatus is removed.

Figure 8:
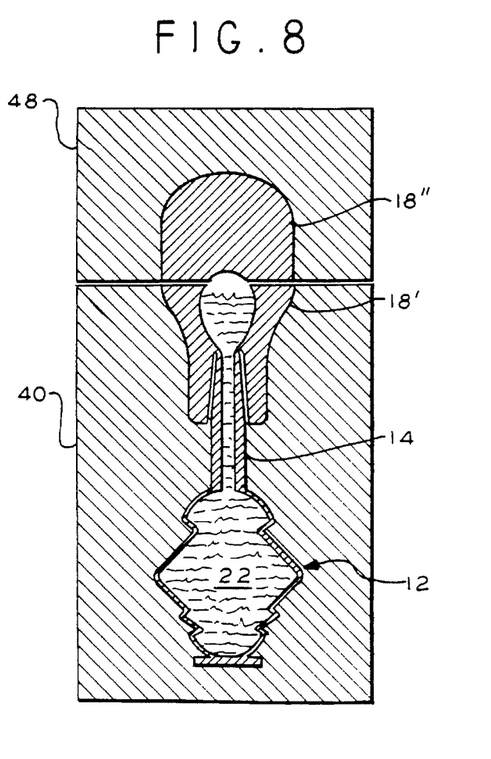
FIG. 8 is a vertical cross-sectional view illustrating sealing together of the previously formed two portions of the plungerless syringe.

The upper portion 18" of the tab 18 (FIGS. 1–3) may be suitably formed from the noted plastic materials such as by blow molding in a suitable mold 48. The tab portion 18" is formed to include a portion 30" of the over-fill chamber 30 (FIGS. 1–3). Thereafter, the molds 48 and 40 are brought into engagement as shown in FIG. 8 and the portions 18' and 18" of the tab 18 are integrated or sealed together with suitable heat and pressure, or by sonic welding, as known to the art for joining separate plastic parts.

Figures 9, 10:
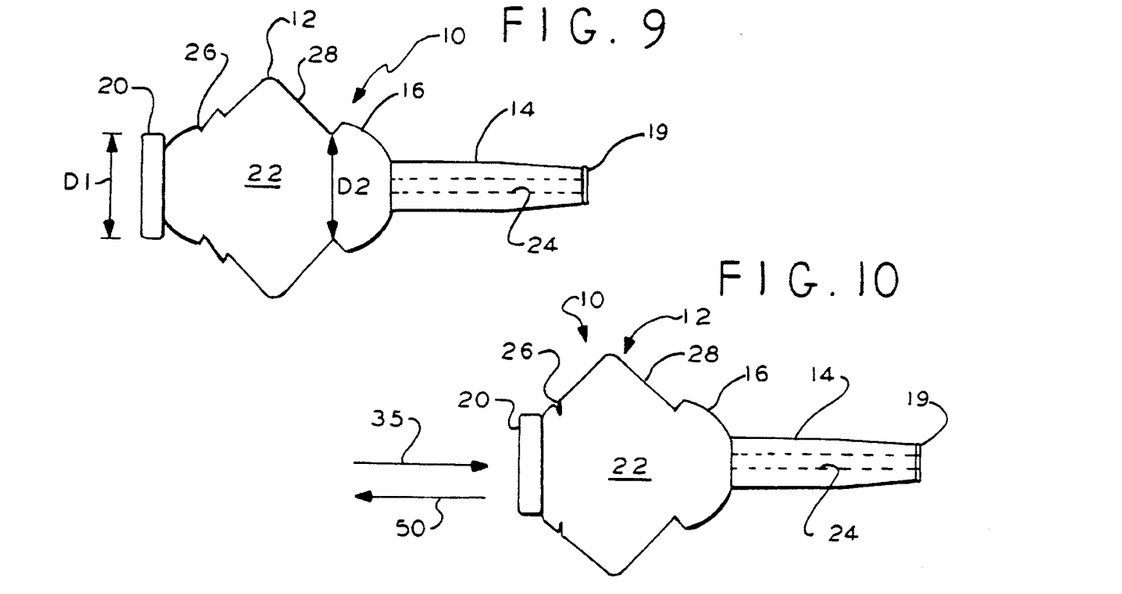
FIG. 9 is a side view of the plungerless syringe of the present invention with the tab portion removed in preparation for fluid expulsion or injection.
FIG. 10 illustrates the partial collapse of the bellows in the fluid purge stage.

Referring now to FIGS. 9–12 and in detail to the operation of the plungerless syringe 10 of the present invention, it will be assumed that the tab 18 has been broken away or removed from the cannula tip 19 as shown in FIG. 3 and described above and that the cannula tip 19 has been inserted, for example, into the hub portion 33 of the needle 34 shown in FIG. 4; the needle 34 is not shown in FIGS. 9–12 for convenience of illustration. The syringe 10 will be grasped or held by the user as shown in FIG. 4 and inwardly acting force 35 will be applied to the push-button portion 20 as shown in FIG. 10 to collapse the rearward or first bellows portion 26 and expel a portion of the fluid contained in the internal chamber 22 through the cannula passageway 24 and the needle 34 (FIG. 4). Collapse of the rearward bellows portion 28 provides the purge stage noted above and expels air present in the needle 34 or other fluid delivery device which may be attached to the cannula tip 19. After the purge stage, the tab portion 20 may be grasped by the fingers of the other hand of the user (not shown) to pull the tab portion 20 outwardly or rearwardly as indicated by the arrow 50 in FIG. 10, to re-expand or uncollapse the first bellows portion 26 into the uncollapsed position shown in FIG. 9 to reflux or aspirate the fluid expelled in the purge stage and to draw into at least the cannula passageway 24 a sample of blood to determine if the tip of the needle is properly inserted into a blood vessel. Accordingly, it will be understood that the tab 20 is also an aspiration tab and that the re-expansion of the first bellows portion 26 is an aspiration stage.

Figure 11:
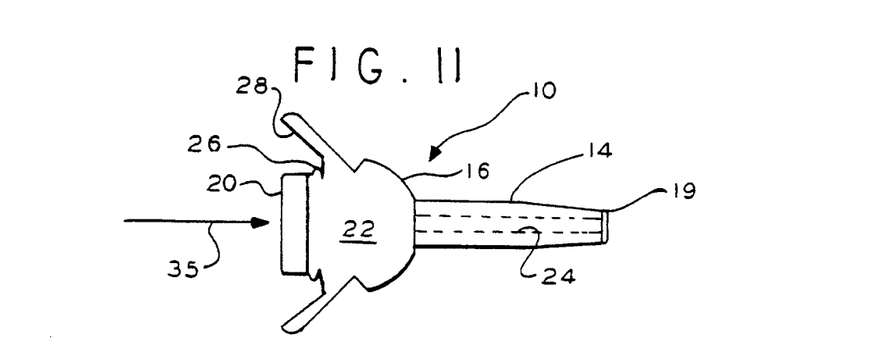
FIG. 11 illustrates the further collapse of the bellows in the fluid flush stage.

Thereafter, the inwardly directed force 35 is applied again to the tab 20 as illustrated in FIG. 11 to re-collapse the first bellows portion 26 and to collapse the second bellows portion 28 in the flush stage to expel the fluid contained in the chamber 22 through the cannula passageway 24 and through the needle 34 (FIG. 4).

Referring again to FIG. 9, it will be noted that the tab portion 20 is provided with a diameter D1 and that the rearward portion of the dome portion 16 provided with a diameter D2. The diameter D1 is larger than the diameter D2 and in an embodiment of the plungerless syringe of the present invention the diameter D1 is 0.458 inch and the diameter D2 is 0.418 inch. Accordingly, upon continued application of the force 35 after collapse of the bellows portion 12, FIG. 12, the disk-like or push-button portion 20 is forced and wedged into the dome portion 16 to maintain the bellows portion 12 collapsed, and thereby prevent unintentional reflux of previously expelled fluid into the syringe 10; it will be noted from FIG. 12 that upon collapse the bellows portion 12 is substantially contained in the dome portion 16.

Referring again to FIG. 2, it will be noted that the forward bellows portion 28 is defined by a wall having a thickness T1 and that the rearward bellows portion 26 is defined by a wall having a thickness T2 and it will be understood that the thickness T2 is less than the thickness T1. This difference in wall thickness facilitates collapse of the bellows portion 12 by inversion, instead of compression, as shown particularly in FIG. 12. It has been discovered that collapse of the bellows portion 12 by inversion, instead of compression, is highly desirable because it reduces the possibility of unintentional fluid reflux subsequent to complete collapse of the bellows portion 12. Such inadvertent reflux is undesirable, since it may result in reduced fluid delivery efficiency and can undesirably draw blood into the needle and syringe after total bellows collapse or undesirably draw previously expelled fluid and blood into the fluid delivery device, such as a needle or catheter, connected to the syringe, and such inadvertent reflux can create a vacuum in the needle or other fluid delivery intravenous access device, such as a catheter, which may result in blood reflux into the catheter. Reflux is undesirable because it may result in clot formation within the catheter line.

Figure 12:
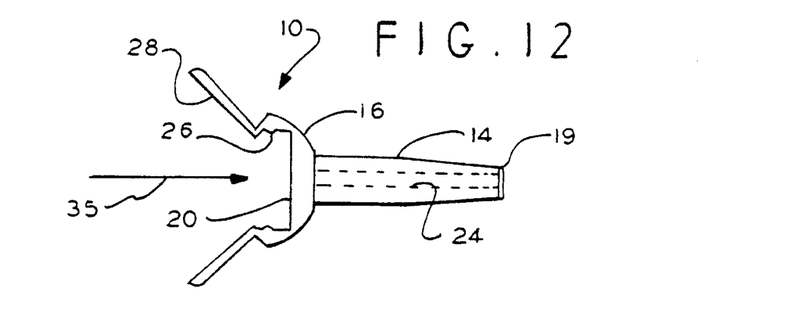
FIG. 12 illustrates the mechanical snap-fit for maintaining the bellows fully collapsed to permit unintentional fluid reflux.
Figure 13:
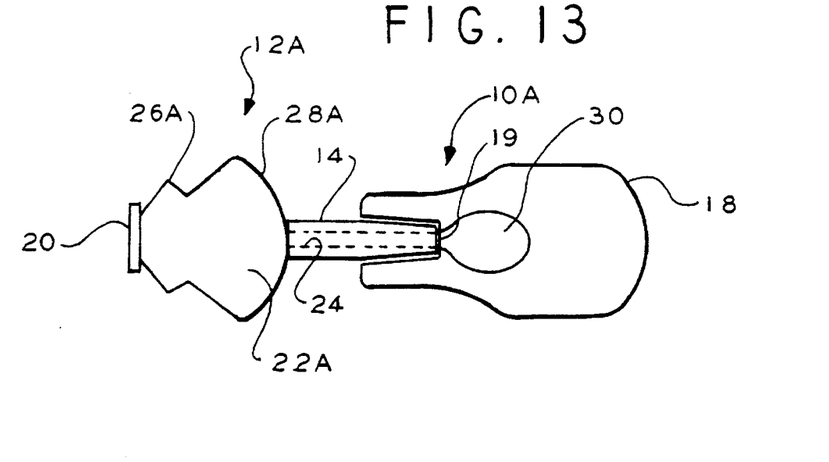
FIG. 13 is a side view of an alternate embodiment of a plungerless syringe embodying the present invention.

It will be still further understood that the bellows portion 12 of the plungerless syringe 10 of the present invention may be fully collapsed in a single step into the position shown in FIG. 12 without the sequential performance of the purge stage and then the flush stage and without the performance of the aspiration step noted above.

Referring now to FIGS. 13–17, an alternate embodiment plunger syringe embodying the present invention is shown and indicated by general numerical designation 10A. It will be generally understood that the plungerless syringe 10A is substantially similar to the earlier embodiment plungerless syringe 10 and performs substantially the same function in substantially the same way except that plungerless syringe 10A collapses, not by inversion, but instead by compression, does not include the dome portion 16 and the wall thickness of the bellows portion 28A is substantially uniform and does not vary in thickness as does the wall thickness of the bellows portion 28 of embodiment 10. Accordingly, for convenience of presentation and understanding, structural elements comprising plungerless syringe 10A which are the same as the structural elements in plungerless syringe 10 are given the same numerical designations and have the same function.

The bellows portion 12A includes a first or rearward portion 26A and a second or forward bellows portion 28A and is made of a suitable substantially transparent flexible plastic material as described above for the construction of the bellows 12.

Referring to FIGS. 14–17, the rearward or first bellows portion 26A collapses by compression upon the application of the force 35 to the push-button 20 and, as with the first bellows portion 26 of embodiment 10, such collapse expels a portion of the fluid contained in the internal chamber 22A provided by the first and second bellows portions for the same purpose as described above. Afterwards, as explained above, the push-button 20 may be pulled rearwardly by the force 50 shown in FIG. 15 to reflux a portion of the previously expelled fluid as described above and for the same reason. A further application of the force 35, FIGS. 16 and 17, expels the balance of the fluid contained in the chamber 22A and the bellows portion 28A, including first and second bellows portions, collapses by compression into the final expulsion position shown in FIG. 17.

It will be further understood that the plungerless syringe embodiment 10A may be made in the same manner as illustrated above for embodiment 10 and as described above and illustrated in FIGS. 5–8.

Significantly, it will be understood that the removable or break-away tab 18 of embodiment 10A performs the same over-fill and head space isolation function as the correspondingly numbered tab-portion 18 of FIGS. 1–3.

Figure 14:
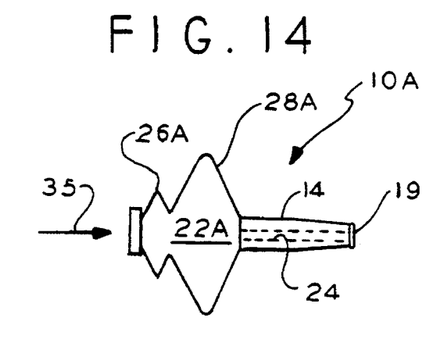
FIG. 14 is a side view of the alternate embodiment of the plungerless syringe of FIG. 13 with the tab portion removed in preparation for fluid expulsion or injection.
Figure 15:
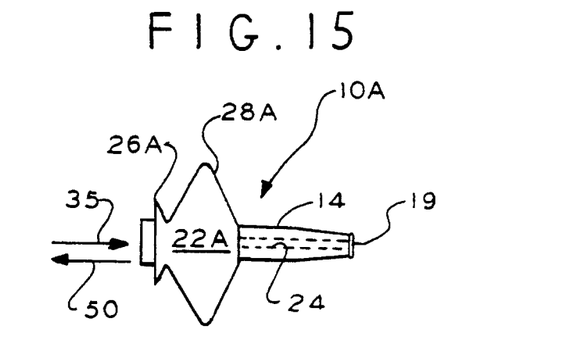
FIG. 15 illustrates the partial collapse of the bellows in the fluid purge stage.
Figure 16:
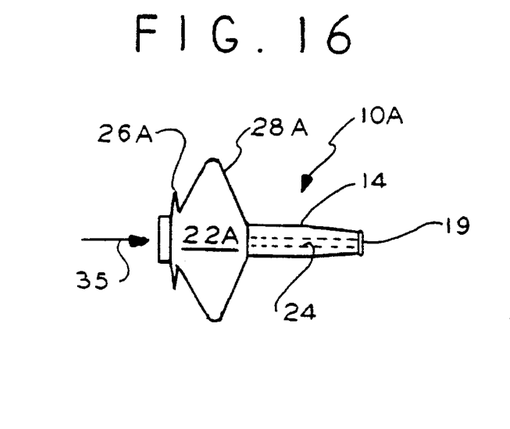
FIG. 16 illustrates a further collapse of the bellows in the fluid flush stage.
Figure 17:
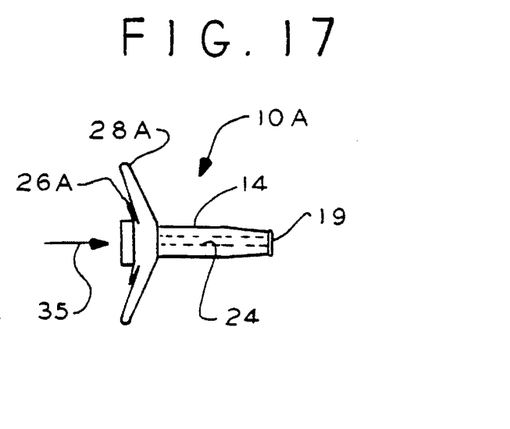
FIG. 17 illustrates the position of the bellows in the final collapse stage.

Referring again to FIGS. 1–3 and 13, it will be noted that the tab 18 is relatively large in size and flange-like in shape and the size of the tab 18 discourages touch contamination of the tip 19 of the cannula 14 upon the tab 18 being removed as shown in FIGS. 3 and 14. The bulb shape of the over-fill tab chamber 30 also discourages touch contamination by distancing the figures from the luer tip.

It will be still further understood that while it is possible for the tab 18 to be removed from the tip of the cannula 14 with the plungerless syringe oriented in a horizontal position wherein, of course, the head space could migrate to the bellows portion 22, this is highly unlikely since the loss of fluid from the syringe would be obvious to a user and a user will naturally or normally orient the plungerless syringes 10 and 10A in the vertical position with tab 18 extending upwardly and will do so through the natural inclination of a person opening a fluid filled container to open the container in the vertical position to prevent fluid spillage. Thus, upon the plungerless syringes 10 and 10A of the present invention being filled as described above and oriented vertically with the tab extending upwardly, the head space will reside in the over-fill chamber 30 of the tab 18 and air in the contained fluid will migrate into the over-fill chamber 30. Accordingly, upon the tab being removed with the syringe being oriented in the vertical position, the bellows chambers 22 and 22A and the passageway 24 of the cannula 14 will be filled with fluid containing substantially no air and the risk of an air embolism will be substantially eliminated. Lastly, it will be understood that by eliminating physically separate or physically distinct parts, such as a separate plunger, the plungerless syringe of the present invention renders it suitable for gamma irradiation sterilization.

Combination apparatus embodying the present invention and for expelling, ejecting or injecting a fluid, viz., a liquid is illustrated in FIGS. 18–24. Referring generally to such FIGS., and in particular to FIG. 18, such combination apparatus of the present invention is indicated generally by numerical designation 60. Combination 60 may include a generally transparent plungerless syringe indicated by general numerical designation 70 and an injector or injector holder indicated by general numerical designation 80; injector 80 may be referred to as collapsing force applying apparatus or means and applies force to the plungerless syringe 70 to expel or eject liquid from the syringe or inject liquid into liquid receiving apparatus such as the needle 34 in FIG. 4.

Plungerless syringe 70 may be, for example, plungerless syringe 10 or plungerless syringe 10A illustrated in the earlier FIGS. and described above. For convenience of presentation, plungerless syringe 70 is shown as being substantially similar to plungerless syringe 10 and performs substantially the same function in substantially the same way as plungerless syringe 10 except that plungerless syringe 70 is operated by the injector or force applying means 80. Accordingly, for convenience of presentation and understanding, structural elements comprising the plungerless syringe 80 which are the same as the structural elements in plungerless syringe 10 are given the same numerical designations and have the same function.

Figures 18, 18A, 19:
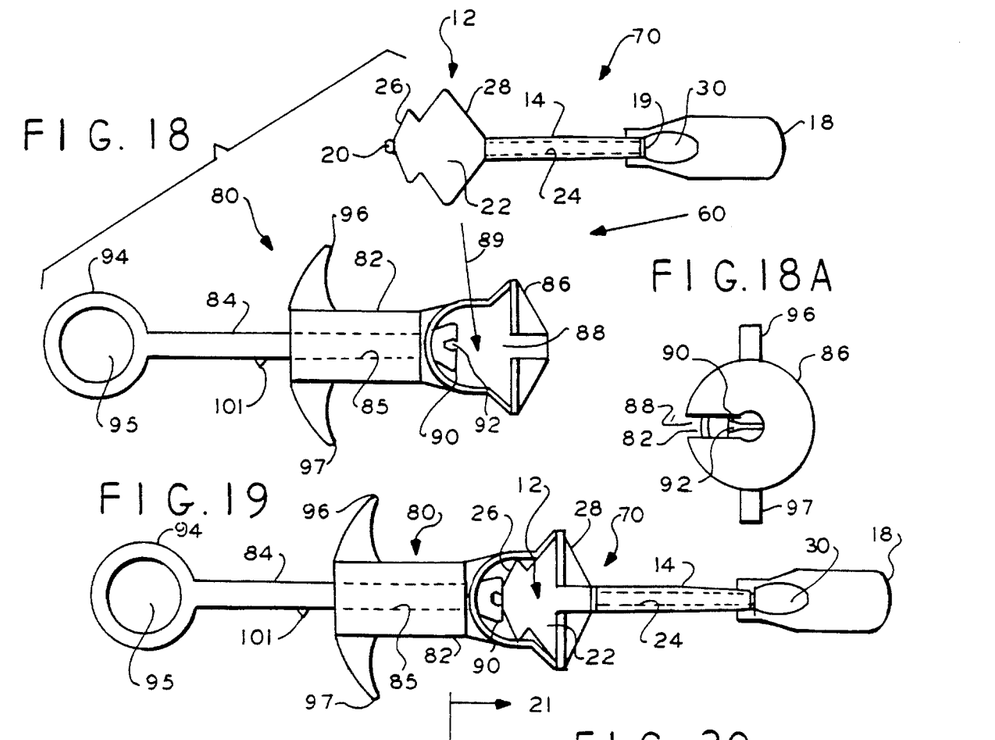
FIG. 18 is a composite view illustrating the combination plungerless syringe and injector or injector holder of the present invention.
FIG. 18A is a right end view of the injector holder shown in FIG. 18.
FIG. 19 is an assembly view illustrating the assembly of the combination plungerless syringe and injector or injector holder of the present invention.
Figure 20:
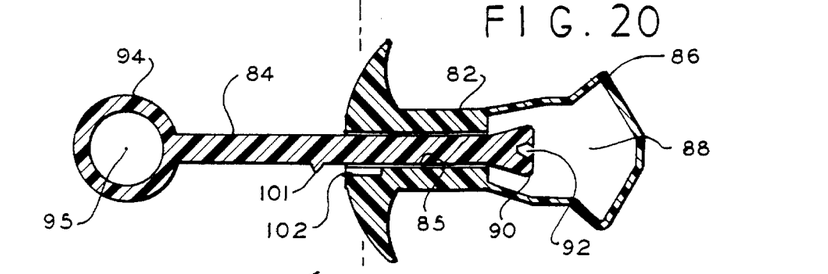
FIG. 20 is a vertical cross-sectional view of the injector holder of the present invention.
Figure 21:
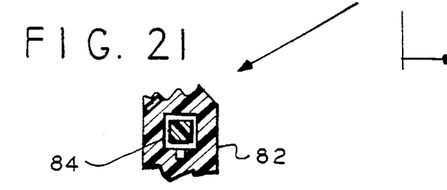
FIG. 21 is a transverse cross-sectional view taken generally along the lines 21—21 in FIG. 20 in the direction of the arrows.

Injector or force applying apparatus 80 includes a cylinder 82 and a plunger 84 mounted slidably in a passageway 85 formed in the cylinder for sliding advancement into and for sliding retraction out of the cylinder; the structural and functional relationship between the cylinder 82 and plunger 84 are shown in detail in cross-sectional FIGS. 20 and 21. The forward portion of the cylinder 82 is provided with a hollow generally semi-spherical receptacle or receiving member 86 generally complementary in shape to and for receiving the bellows portion 12 and push button 20 of the syringe 70, with the cannula portion 14 extending outwardly therefrom, as shown in FIG. 19. The receptacle 86 is provided with an opening, e.g. a lateral opening, 88, FIGS. 18 and 18A, which permits the bellows portion 12 and push button 20 of the syringe 80 to be received by or inserted into the receptacle 86 as indicated by the arrow 89 in FIG. 18.

The forward end of the plunger 84 is provided with an engaging member 90, FIG. 18, which is provided with an opening 92 generally complementary in shape, or cross-sectional shape, to, and for releasably, receiving the syringe push button 20 as shown in FIG. 19; the push button 10 may be cylindrical or rectangular.

The injector or force applying apparatus 80 is for being operated by a user and is for having manual force supplied directly thereto by the user which force, or bellows collapsing force, is transferred to the syringe bellows 12 by the plunger 84. To facilitate handling in the application of manually applied force to the injector or force applying apparatus 80, the rearward portion of the plunger 84 is provided with an annular member 94 provided with an opening 95 for receiving the thumb of a user and the rearward portion of the cylinder 82 is provided with a pair of opposed generally curved gripping members 96 and 97 for receiving the middle and index fingers of the user. Upon the thumb of the user being placed in the opening 95 and the middle and index fingers of the user being placed on the gripping members 96 and 97, the thumb and fingers are squeezed together to directly apply manual force to the injector or apparatus 80 which, as noted above, is transferred to the syringe bellows 12 by the plunger 84 to collapse the bellows and expel or eject liquid received or contained in the syringe out of or through the cannula portion 14.

The detailed structure of the cylinder 82, plunger 84 and receptacle 86 may be better seen by reference to the cross-sectional views in FIGS. 20 and 21. It will be understood that the cylinder 82, receptacle 86 and plunger 84 may be made by suitable injection molding and may be made of a suitable material such as for example polypropylene; the cylinder 82 may be molded in two pieces, e.g. split transversely or horizontally as viewed in FIGS. 18 and 19 thereby permitting assembly of the plunger 84 to the cylinder after which the two pieces of the cylinder may be suitably bonded together such as for example by a suitable adhesive. Accordingly, it will be understood that the plunger 84 may be provided with an outwardly extending generally flexible tab 101 and the cylinder 82 may be provided with an inwardly extending slot 102 for receiving the flexible tab 101 in a slightly wedged sliding engagement upon the plunger 84 being advanced into the cylinder passageway 85. It will be understood that the flexible tab 101 and the slot 102 in conjunction with the plunger 84 and cylinder 82 cooperate to provide staged apparatus for applying first and second stages of ejection force to the syringe push button 20 and thereby to the syringe bellows 12 to collapse the first or rearward bellows portion 26 and to subsequently collapse the second or forward bellows portion 28, note such bellows portions in FIGS. 18 and 19.

Figure 22:
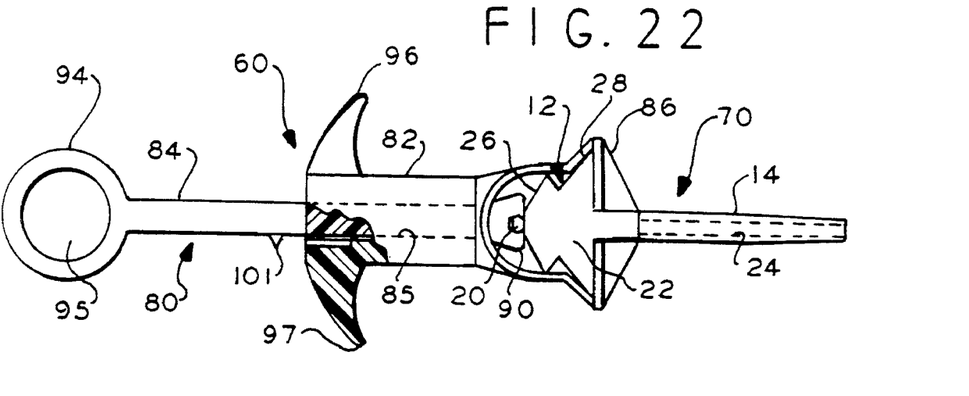
FIGS. 22–24 are diagrammatical illustrations of the function or operation of the combination plungerless syringe and injector holder of the present invention.
Figure 23:
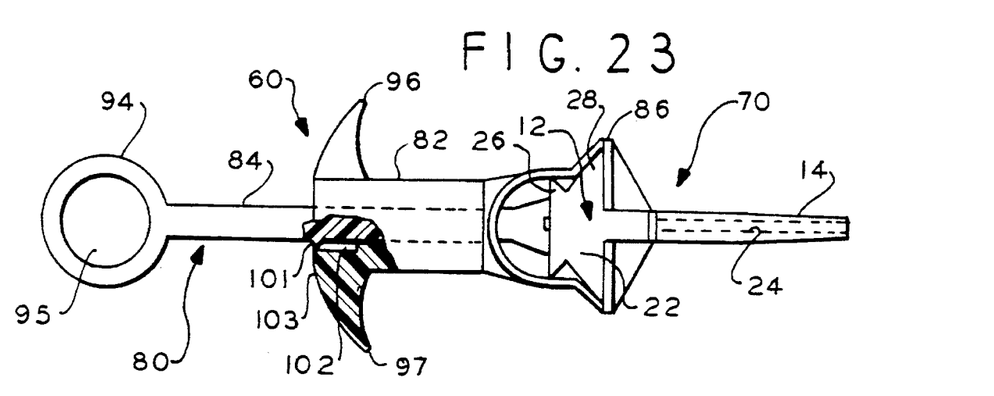
Figure 24:
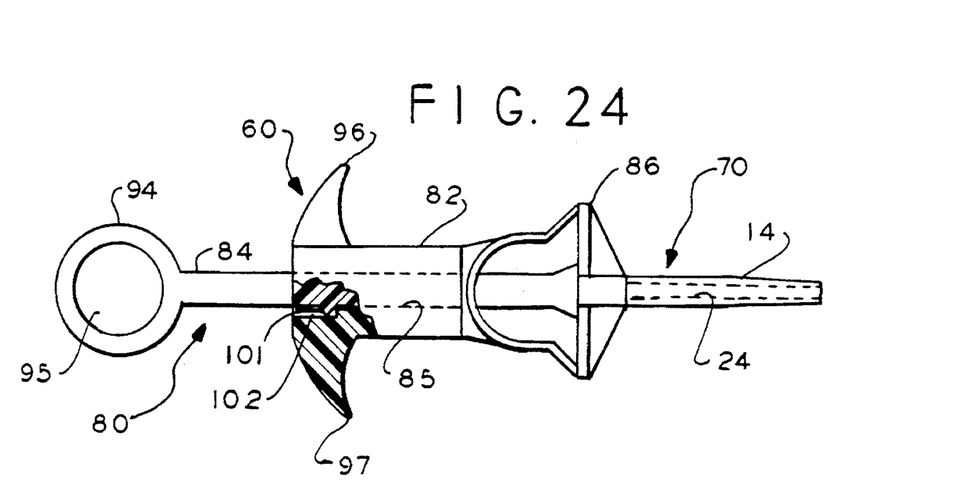

Referring now to FIGS. 22–24 and to the operation of the combination apparatus 60 of the present invention, it will be presumed that the bubbleless syringe 70 has been filled with a liquid, such as for example a suitable saline solution, and that the tab 18 (FIGS. 18 and 19) has been removed as described above in connection with plungerless syringes 10 and 10A and that the cannula tip 19 has been inserted into a needle or the typical extension of an in-dwelling catheter. It will be further presumed that the syringe bellows portion 12 and push button 20 have been received within the receptacle 86, that the cannula portion 14 is extending outwardly from the receptacle and that the forward portion 90 of the plunger 84 is in engagement with the push button 20. The user will advance the plunger 84, as described above, into the cylinder passageway 85 until the flexible tab 101 engages the portion 103, FIG. 23, of the cylinder 82 surrounding the slot 102. Upon such engagement, a tactile indication or signal is provided to the user that the plunger 84 has been advanced sufficiently into the cylinder 82 to collapse the first or rearward bellows portion 26 to expel or eject a portion of the liquid received within the syringe through the cannula portion 14 to purge air contained in liquid receiving apparatus connected to the outer end of the cannula portion 14, such as for example, the needle 34 shown in FIG. 4 or the extension of an in-dwelling catheter and thereby the catheter. Subsequently, the user may retract the plunger 84 from the cylinder 82 by applying a pulling force with the user's thumb inserted in the opening 95 to retract the plunger 84 to substantially the position shown in FIG. 23 which causes the forward portion 90 of the plunger to apply a pulling force to the syringe push button 20 to re-expand the first or rearward bellows portion 26 and aspirate or reflux the previously expelled liquid to facilitate determination of the continuity of a liquid path including the syringe internal chamber 22, cannula portion passageway 24 and liquid receiving apparatus connected to the outer end of the cannula portion such as for example the above-noted needle 34 shown in FIG. 4 or the extension of an in-dwelling catheter residing in a patient's blood vessel. More specifically, upon the needle 34 or catheter being inserted into the blood vessel of a patient, retraction of the plunger 84 and aspiration or reflux of the previously expelled liquid permits the user to observe the intentional aspiration or reflux of the previously expelled fluid and the withdrawing of blood from a blood vessel into which the needle 34 or catheter is inserted thereby determining that the tip of the needle or the catheter is properly inserted into a blood vessel; the blood observation by the user being permitted by the transparency of the plungerless syringe 70.

Thereafter, as illustrated in FIG. 24, the user advances the plunger 84 into the cylinder passageway 85 until the plunger flexible tab 101 engages the end of the slot 102 which engagement provides a second tactile signal or indication to the user that the plunger has been advanced into the cylinder 82 sufficiently to collapse both the first or rearward bellows portion 26 and the second or forward bellows portion 28 to flush or substantially completely expel or eject the fluid from the syringe through the cannula passageway 24 to liquid receiving apparatus such as the above-noted needle or catheter; for convenience of illustration and discernment the tab 101 is not shown in actual engagement with the end of the slot 102 in FIG. 24.

Thereafter, the plunger 84 is withdrawn by the user and the used or expired plungerless syringe 70 is removed from the cylinder receptacle 86 and the injector or force applying apparatus 80 may be reused or disposed of.

It will be understood that the present invention is directed to the combination of a plungerless syringe and injection holder or apparatus for applying ejection force to the syringe and also relates to a separate invention of the injector holder or apparatus for ejecting fluid from a plungerless syringe.

It will be further understood by those skilled in the art that many modifications and variations may be made in the present invention without departing from the spirit and the scope thereof.

What is claimed is:

1. Combination apparatus for ejecting liquid, comprising:
   a plungerless syringe having opposed ends, a cannula portion at one end, ejection force receiving means at the other end and a collapsible bellows portion intermediate said ends, said syringe for receiving liquid to be ejected through said cannula portion upon said bellows portion being collapsed; and
   ejection force applying means including receptacle means for releasably receiving at least said ejection force receiving means and said bellows portion to permit said ejection force applying means to apply ejection force to said ejection force receiving means to collapse said bellows portion and cause liquid received in said syringe to be ejected through said cannula, said receptacle means comprising a hollow generally semi-spherical member generally complementary in shape to said bellows portion and provided with a lateral opening for permitting at least said bellows portion to be inserted laterally into said member and for permitting said cannula portion to extend outwardly from said member.

2. The combination according to claim 1 wherein said bellows portion includes a purge portion adjacent said ejection force receiving means and a flush portion intermediate said purge portion and said cannula portion, and wherein said ejection force applying means includes staged means for applying first and second stages of ejection force to said ejection force receiving means, upon said staged means applying said first stage of ejection force to said ejection force receiving means said purge portion of said bellows portion being collapsed to eject a portion of the liquid received within said syringe and upon said staged means applying said second stage of ejection force to said ejection force receiving means said flush portion of said bellows being collapsed to eject the remainder of the liquid received within said syringe.

3. The combination according to claim 2 wherein said ejection force applying means includes tactile indicating means for providing tactile indications to a user of said combination to indicate that said ejection force applying means has applied said first and second stages of ejection force to said ejection force receiving means.

4. The combination according to claim 1 wherein said bellows portion includes a purge portion and a flush portion intermediate said purge portion and said cannula portion, and wherein said ejection force applying means includes staged means for applying first and second stages of ejection force to said bellows portion, upon said staged means applying said first stage of ejection force to said bellows portion said purge portion of said bellows portion being collapsed to eject a portion of the liquid received within said syringe and upon said staged means applying said second stage of ejection force to said bellows portion said flush portion of said bellows being collapsed to eject the remainder of the liquid received within said syringe.

5. Combination apparatus for ejecting liquid, comprising:

a plungerless syringe including a cannula portion and a bellows portion, said syringe for receiving the liquid which is ejected through said cannula portion upon said bellows portion being collapsed; and ejection force applying means including hollow generally semi-spherical receptacle means generally complementary in shape to at least said bellows portion of said syringe and for releasably receiving at least said bellows portion of said syringe and for permitting said cannula portion to extend outwardly therefrom, upon at least said bellows portion being received within said receptacle means, said ejection force applying means for applying force to said bellows portion to collapse said bellows portion and eject the liquid through said cannula portion, said receptacle means provided with a lateral opening through which at least said bellows portion is inserted into said receptacle means.

6. The combination according to claim 5 wherein said combination is for being operated by a user and wherein said ejection force applying means is provided with means for receiving a manually applied force from the user and for transferring said manually applied force to said bellows portion to collapse said bellows portion.

7. The combination according to claim 5 wherein said ejection force applying means is provided with facilitating means for facilitating holding of said force applying means by the user and for facilitating the application of manually applied force to said ejection force applying means by the user.

8. The combination according to claim 5 wherein said ejection force applying means includes a cylinder and a plunger mounted slidably in said cylinder for advancement into said cylinder, said plunger including a forward portion for being advanced into said receptacle means to apply said collapsing force to said bellows portion upon said plunger being advanced into said cylinder.

9. The combination according to claim 8 wherein said syringe includes a push button portion adjacent said bellows portion and opposite said cannula portion and wherein said forward portion of said plunger is provided with engaging means providing an opening generally complementary in shape to said push button portion and for receiving said push button portion to cause said forward portion of said plunger to releasably engage said push button portion and facilitate the application of said collapsing force to said bellows portion through said forward portion of said plunger and said push button portion of said syringe.

10. The combination according to claim 8 wherein said plunger includes a rearward portion provided with an annular member for receiving the thumb of the user and wherein said cylinder includes a rearward portion provided with a pair of opposed curved members for receiving the fingers of the user and wherein said annular member and said curved members comprise facilitating means for facilitating the application of manually applied force to said plunger by the user.

11. The combination according to claim 5 wherein said combination is for being operated by a user and wherein said ejection force applying means are provided with tactile indicating means for providing a tactile indication to the user that said bellows portion has been collapsed.

12. Combination apparatus for ejecting liquid, comprising:

a plungerless syringe including a bellows portion and a cannula portion, said bellows portion including a first bellows portion and a second bellows portion intermediate said first bellows portion and said cannula portion, said cannula portion for being connected to liquid receiving apparatus; and ejection force applying means including receptacle means for receiving at least said bellows portion of said syringe and for permitting said cannula portion to extend outwardly therefrom, said ejection force applying means for applying a first pushing force to said first bellows portion to collapse said first bellows portion and expel a portion of the liquid received within said syringe through said cannula portion to purge air contained in said liquid receiving apparatus, said ejection force applying means for applying a pulling force to said first bellows portion to re-expand said first bellows portion and aspirate at least a portion of the previously expelled liquid to facilitate determination of a continuity of a fluid path including at least said cannula portion and said liquid receiving apparatus, and said ejection force applying means for applying a second pushing force to said first and second bellows portions to collapse said first and second bellows portion and to expel the liquid through said cannula portion into said liquid receiving apparatus, said receptacle means comprising a hollow generally semi-spherical member generally complementary in shape to at least said bellows portion of said syringe, said member provided with a lateral opening permitting at least said bellows portion to be inserted laterally into said member and permitting said cannula portion to extend outwardly from said member.

13. The combination according to claim 12 wherein said combination is for being operated by a user and wherein said ejection force applying means is provided with tactile indicating means for providing a tactile indication to the user that the first pushing force has been applied to said first bellows portion and for providing a second tactile indication to said user that said second pushing force has been applied to said first and second bellows portions.

14. Combination apparatus for ejecting liquid, comprising:

a plungerless syringe including a cannula portion and a bellows portion and which syringe is for receiving liquid which is ejected through the cannula portion upon the bellows portion being collapsed;

ejection force applying means including receptacle means for releasably receiving at least said bellows portion of said syringe and for permitting said cannula portion to extend outwardly therefrom, upon at least said bellows portion being received within said receptacle means, said ejection force applying means for applying force to said bellows portion to collapse said bellows portion and eject the liquid through said cannula portion, said receptacle means comprise a hollow generally semi-spherical member provided with a lateral opening for permitting at least said bellows portion of said syringe to be inserted laterally into said member and for permitting said cannula portion to extend outwardly from said member;

said ejection force applying means including a cylinder and a plunger mounted slidably in said cylinder for advancement into said cylinder, said plunger including a forward portion for being advanced into said receptacle means to apply said collapsing force to said bellows portion upon said plunger being advanced into said cylinder; and said syringe including a push button portion adjacent said bellows portion and opposite said cannula portion and wherein said forward portion of said plunger is provided with engaging means providing an opening generally complementary in shape to said push button portion and for receiving said push button portion to cause said forward portion of said plunger to releasably engage said push button portion and facilitate the application of said collapsing force to said bellows portion through said forward portion of said plunger and said push button portion of said syringe.

15. The combination according to claim 14 wherein said ejection force applying means is for being operated by a user and wherein said ejection force applying means is provided with means for receiving a manually applied force from the user and for transferring said manually applied force to said bellows portion to collapse said bellows portion.

16. The combination according to claim 15 wherein said ejection force applying means is provided with facilitating means for facilitating holding of said ejection force applying means by the user and for facilitating the application of said manually applied force to said ejection force applying means by the user.

17. The combination according to claim 16 wherein said plunger includes a rearward portion provided with an annular member for receiving the thumb of the user and wherein said cylinder includes a rearward portion provided with a pair of opposed curved members for receiving the fingers of the user and wherein said annular member and said curved members comprise said facilitating means.

18. The combination according to claim 14 wherein said combination is for being operated by a user and wherein said ejection force applying means are provided with tactile indicating means for providing a tactile indication to the user that said bellows portion has been collapsed.

19. The combination according to claim 14 wherein said bellows portion includes a purge portion and a flush portion intermediate said purge portion and said cannula portion, and wherein said ejection force applying means includes staged means for applying first and second stages of ejection force to said bellows portion, upon said staged means applying said first stage of ejection force to said bellows portion said purge portion of said bellows portion being collapsed to eject a portion of the liquid received within said syringe and upon said staged means applying said second stage of ejection force to said bellows portion said flush portion of said bellows being collapsed to eject the remainder of the liquid received within said syringe.

* * * * *